(12) United States Patent
Boretzki (10) Patent No.: US 8,666,084 B2
(45) Date of Patent: Mar. 4, 2014

(54) METHOD AND ARRANGEMENT FOR TRAINING HEARING SYSTEM USERS

(75) Inventor: Michael Boretzki, Rüti (CH)

(73) Assignee: Phonak AG, Stafa (CH)

( * ) Notice: Subject to any disclaimer, the term of this patent is extended or adjusted under 35 U.S.C. 154(b) by 956 days.

(21) Appl. No.: 12/667,244

(22) PCT Filed: Jul. 6, 2007

(86) PCT No.: PCT/EP2007/056913
§ 371 (c)(1),
(2), (4) Date: Dec. 30, 2009

(87) PCT Pub. No.: WO2007/113339
PCT Pub. Date: Oct. 11, 2007

(65) Prior Publication Data
US 2010/0183161 A1 Jul. 22, 2010

(51) Int. Cl.
H04R 25/00 (2006.01)
(52) U.S. Cl.
USPC .............................. 381/60; 381/312; 381/314
(58) Field of Classification Search
USPC ............... 381/56, 58, 60, 312, 314, 315, 320, 381/321, 71.6, 104; 600/559; 73/585
See application file for complete search history.

(56) References Cited

U.S. PATENT DOCUMENTS

| 6,574,342 B1 * | 6/2003 | Davis et al. ................... 381/314 |
| 2005/0094822 A1 * | 5/2005 | Swartz ............................. 381/56 |

FOREIGN PATENT DOCUMENTS

| DE | 102005034381 A1 | 1/2007 |
| WO | 03032681 A1 | 4/2003 |
| WO | 2007042043 A2 | 4/2007 |

OTHER PUBLICATIONS

International Search Report for PCT/EP2007/056913 dated Apr. 4, 2008.

* cited by examiner

*Primary Examiner* — Huyen D Le
(74) *Attorney, Agent, or Firm* — Pearne & Gordon LLP (57) ABSTRACT

The inventor has found that a considerable portion of hearing system users have a considerable lack of understanding the effect of adjusting adjustable audio processing parameters of the hearing system. Therefore, the method according to the invention comprises the steps of a) playing a first test sound to a user of a hearing system;

r) receiving user input from said user in reaction to step a);

s) interpreting said user input as a request for selecting and/or adjusting at least one audio processing parameter of a signal processing unit;

h) calculating—based on said request obtained in step s), and in dependence of said first test sound played to said user—at least one value, which is related to said user's ability to make use of one or more adjustable audio processing parameters of said hearing system.

This method can be used for improving said user's ability to make use of one or more adjustable audio processing parameters of said hearing system. A corresponding arrangement is disclosed, too.

23 Claims, 4 Drawing Sheets

METHOD AND ARRANGEMENT FOR TRAINING HEARING SYSTEM USERS

TECHNICAL FIELD

The invention relates to the field of hearing devices. It relates to methods, arrangements and a use of said method according to the patent claims.

Under a hearing device, a device is understood, which is worn in or adjacent to an individual's ear with the object to improve the individual's auditory perception. Such improvement may also be barring acoustic signals from being perceived in the sense of hearing protection for the individual. If the hearing device is tailored so as to improve the perception of a hearing impaired individual towards hearing perception of a "standard" individual, then we speak of a hearing-aid device. With respect to the application area, a hearing device may be applied behind the ear, in the ear, completely in the ear canal or may be implanted.

A hearing system comprises at least one hearing device. In case that a hearing system comprises at least one additional device, all devices of the hearing system are operationally connectable within the hearing system. Typically, said additional devices such as another hearing device, a remote control or a remote microphone, are wearable by said individual.

Audio signals are electrical signals, of digital and/or analog type, which represent sound.

BACKGROUND OF THE INVENTION

Today's digital hearing devices provide for vast signal processing capabilities. In order to allow for an individual adaptation of the hearing device to the hearing needs and preferences of a hearing device user, the way said signal processing takes place in the hearing device is dependent on several audio processing parameters. Some of these audio processing parameters are meant to be adjusted by the user (adjustable audio processing parameters; more precisely user-adjustable audio processing parameters). E.g., a hearing device usually allows the user to adjust the general output level of the hearing device, typically by toggling a volume toggle switch or by turning a volume control wheel. And, most of today's digital hearing devices have several hearing programs, which are basically sets of audio processing parameters to be used in said different acoustic situations, wherein most of said hearing devices allow the user to select a hearing program in dependence of the current acoustic situation, e.g., by manipulating a program switch. In case of a hearing system comprising a remote control, it can be provided that the before-mentioned and/or other audio processing parameters can be adjusted by means of said remote control, which for this reason may comprise corresponding and/or further user controls.

The inventor has found that a considerable portion of hearing system users have a considerable lack of understanding the effect of adjustments of available adjustable audio processing parameters.

Therefore, it is desirable to improve a hearing system user's ability to make use of one or more adjustable audio processing parameters of the hearing device.

In DE 10 2005 034 381 A1, it is suggested to provide user controls of a hearing-aid device with a new function, so as to use the hearing-aid device for new purposes. In particular, it is suggested to integrate the hearing-aid device in a software-based gaming environment and to use the user controls of the hearing-aid device as input means for giving input to such a software game. This way, the hearing-aid device user shall get acquainted and used to handling the (physical) user controls of the hearing-aid device. This extended use of a hearing-aid device shall improve the acceptance of hearing-aid devices.

SUMMARY OF THE INVENTION

Therefore, one object of the invention is to create a method and a corresponding arrangement, which allow to improve a hearing device user's ability to make use of one or more adjustable audio processing parameters of said hearing device. In addition, a use of said method shall be provided.

The inventor has also found that many hearing system users do, in practice, still not sufficiently understand, how to properly make use of the hearing system's adjustable audio processing parameters, even after having been thoroughly instructed during one or two dedicated lessons.

Another object of the invention is to provide a hearing system user with an improved understanding of the hearing system's adjustable audio processing parameters.

Another object of the invention is to provide a possibility for a hearing system user to train how to properly and efficiently use adjustable audio processing parameters of his hearing system.

Another object of the invention is to provide an efficient way to instruct a hearing system user about making proper use of adjustable audio processing parameters for modifying sound perceived by the user through the hearing system.

Another object of the invention is to provide for an effective way to teach and/or train a hearing system user in making good use of adjustable audio processing parameters for creating an improved hearing sensation.

Further objects emerge from the description and embodiments below.

At least one of these objects is at least partially achieved by arrangements, methods and uses according to the patent claims.

The method comprises the steps of
a) playing a first test sound to a user of a hearing system;
r) receiving user input from said user in reaction to step a);
s) interpreting said user input as a request for selecting and/or adjusting at least one audio processing parameter of a signal processing unit;
h) calculating—based on said request obtained in step s), and in dependence of said first test sound played to said user—at least one value, which is related to said user's ability to make use of one or more adjustable audio processing parameters of said hearing system.

Typically, step a) is carried out automatically, in particular upon a request of said user.

Typically, step s) is carried out automatically.

Typically, step h) is carried out automatically.

In one embodiment, steps s) and h) are replaced by the following steps s') and h'):
s') selecting and/or adjusting at least one audio processing parameter of a signal processing unit in response to said user input;
h') calculating—based on said selection and/or adjustment according to step s'), and in dependence of said first test sound played to said user—at least one value, which is related to said user's ability to make use of one or more adjustable audio processing parameters of said hearing system.

Typically, step s') is carried out automatically.

Typically, step h') is carried out automatically.

It is desirable to teach the user to choose the appropriate signal processing parameter(s) for achieving a desired sound modification. If the user has made such selections many times, the recording of these selections allows to analyze whether or not and to which degree the user's ability to make use of one or more adjustable audio processing parameters of said hearing system has improved. From such recordings, a value can be obtained, which is related to said user's know how concerning said adjustable audio processing parameters. If, in step s) and s'), respectively, said input is interpreted as a request for selecting at least one audio processing parameter, said at least one value mentioned in step h) and h'), respectively, can be an indicator for the user's ability to understand the effect of at least this selected audio processing parameter or for the user's ability to make proper choices from available audio processing parameters.

If, in step s) and s'), respectively, said input is interpreted as a request for adjusting said at least one audio processing parameter, said at least one value mentioned in step h) and h'), respectively, can be an indicator for the user's ability to adjust audio processing parameters (in particular the adjusted audio processing parameter) in an effective way.

In one embodiment, said hearing system is used for generating said first test sound. In a different embodiment, said first test sound is generated externally to said hearing system.

In one embodiment, said user input is received by a user interface of said hearing system; typically, a user interface comprises at least one user control manipulable by said user. In a different embodiment, said user input is received externally to said hearing system.

In one embodiment, said at least one parameter of said signal processing unit is adjusted in response to said user input, wherein said signal processing unit is comprised in said hearing system. In a different embodiment, said at least one parameter of said signal processing unit is adjusted in response to said user input, wherein said signal processing unit is externally to said hearing system.

In one embodiment, at least one audio processing parameter of a signal processing unit of said hearing system is adjusted for generating said first test sound. In other words, for generating said first test sound, audio signals are processed in a signal processing unit of said hearing system, and before carrying out step a), at least one audio processing parameter of said signal processing unit is adjusted, so as to process said audio signals with the so-adjusted at least one audio processing parameter.

In one embodiment, said first test sound is generated by a sound generating unit external to said hearing system.

In one embodiment, the method comprises the step of
x) maladjusting at least one parameter of a signal processing unit of said hearing system for letting said user perceive a distorted version of said first test sound.

For example, a sound of a whispering voice could be played at an unnaturally high output level, or the sound of a drum set with cymbals could be played with strongly reduced level of high-frequency components. Even without a second test signal for comparison, the user should preferably select the appropriate audio signal parameter (overall output level and level of high-frequency components, respectively, in the named examples) and/or adjust an appropriate audio signal parameter in the proper way.

The inventor has found out that many hearing system users make only unsatisfactory use of sound modification possibilities, even in the case that there is no choice between several sound modification possibilities. E.g., if in addition to said first test sound, a second test sound is played to the user (cf. step b) below), which is brighter than said first test sound, and the sound brightness can be adjusted by means of a user control, most users tend to decrease the brightness by means of said user control to a small degree only, insufficient to fully compensate the difference between said first and said second test sound. It would rather be desirable to firstly overcompensate, i.e., to reduce the brightness too much, and then increase the brightness again, a bit too much, and develop towards the desired sound (resembling said first sound) in such an oscillating fashion with decreasing oscillation amplitude. This preferred way of adjusting a parameter is also referred to as bracketing and will usually result in a much more precise result, i.e., for a (nearly) full compensation.

Said recording said adjusting of said at least one audio processing parameter allows to monitor the evolution in time of the parameter adjusting. Thus, the user's ability to adjust audio processing parameters in an effective way can be judged by means of such recordings, and appropriate measures (e.g., instruction lessons) can be taken for improving this ability, if necessary.

If a method as put forward so far is carried out repeatedly, it is possible to judge the user's learning/training progress from the evolution in time of said values obtained in steps h) and h'), respectively, i.e., said user's progress concerning the improvement of his know how concerning the adjustable audio processing parameters of his hearing system can be judged therefrom.

In one embodiment, the method comprises the step of
b) playing a second test sound to said user;
wherein said user input is received in reaction to step a) and step b).

The selection of said first test sound and/or of said second test sound and/or of at least one audio processing parameter that is different in processing for obtaining said first and second test sound, respectively, can be a randomized selection. It is also possible to carry out this selection in dependence of at least one of the values mentioned in steps h) and in step h'), respectively. This way, it would for example be possible to train situations, in which the user performed rather poorly so far, more often than situations in which he performed better.

In one embodiment, the method comprises the step of
q) minimizing differences between said first and second test sound by said adjusting said at least one audio processing parameter mentioned in step s) or s').

This step q) is usually carried out by the user. It is, from a didactic point of view, valuable to let a user hear two different sounds with the task to minimize differences between these, in particular if one of the sounds is a "normal" version of a (test) sound and the other (test) sound is a distorted version of the same sound. The task for the user can be to select the appropriate audio signal parameter for minimizing said differences and/or to adjust an audio signal parameter in the right way for minimizing said differences.

In one embodiment, the method comprises the steps of
p) processing said first test sound or—if applicable—said second test sound in the signal processing unit mentioned in step s) or s'), using the at least one audio processing parameter mentioned in step s) or s') adjusted as mentioned in step s) or s'); and
d) playing the correspondingly processed first or second test sound to said user.

This way, the user may have a very good control over what effect said adjusting said at least one audio processing parameter has.

In one embodiment, the method comprises the step of
k) providing said user with information, which depends on said at least one value mentioned in step h) or h').

This way, the user can receive some feedback about the quality of his input. This enhances the training/learning effect.

In one embodiment, the method is a method for improving a hearing system user's ability to make use of one or more adjustable audio processing parameters of said hearing system.

In one embodiment, the method is a method of training said user in making use of one or more adjustable audio processing parameters of said hearing system.

The use according to the invention is a use of a method according to the invention for improving said user's ability to make use of one or more adjustable audio processing parameters of said hearing system.

The arrangement comprises
a hearing system;
a sound generating unit adapted to playing at least one test sound to a user of said hearing system;
a signal processing unit controllable by at least one adjustable audio processing parameter, for processing audio signals;
a first user interface adapted to receiving user input from said user in reaction to said playing of said at least one test sound;
an evaluation unit adapted to interpreting said user input as a request for selecting and/or adjusting said at least one audio processing parameter of said signal processing unit, and adapted to calculating—based on said request, and in dependence of said at least one test sound played to said user—at least one value, which is related to said user's ability to make use of one or more adjustable audio processing parameters of said hearing system.

Such an arrangement can allow to carry out a method according to the invention.

In one embodiment, said hearing system comprises at least one of
said sound generating unit;
said first user interface;
said signal processing unit controllable by said at least one adjustable audio processing parameter.

In one embodiment, the arrangement comprises a control unit adapted to converting said user input into adjustments of at least one audio processing parameter of said signal processing unit.

In one embodiment, the arrangement comprises a storage unit for storing data representative of audio signals from which said at least one test sound is obtainable.

In one embodiment, the arrangement comprises a control unit adapted to maladjusting at least one parameter of a signal processing unit of said hearing system for letting said user perceive a distorted version of said at least one test sound.

In one embodiment, the arrangement comprises a control unit adapted to controlling at least said sound generating unit in such a way, that first, a first test sound is played to said user and then, a second test sound is played to said user.

In one embodiment, said second test sound is obtained by adjusting at least one audio processing parameter of a signal processing unit of said arrangement and processing audio signals in that signal processing unit. Preferably, these audio signals are the same as used for generating said first test sound.

In one embodiment, the arrangement comprises a second user interface, which may be identical with said first user interface and/or may comprise said sound generating unit, for providing said user with information advising said user to minimize differences between said first and said second test sound by said adjusting at least one adjustable audio processing parameter of said signal processing unit.

In one embodiment, the arrangement comprises a second user interface, which may be identical with said first user interface and/or with said second interface and/or may comprise said sound generating unit, for providing said user with information, which depends on said at least one value.

In one embodiment, the arrangement is fully integrated in said hearing system.

In one embodiment, said at least one test sound is generated by a sound generating unit external to said hearing system.

In one embodiment, said arrangement is an arrangement for improving said hearing system user's know how concerning the handling of said hearing system, more particularly of said hearing system's adjustable audio processing parameters.

The advantages of the arrangements and uses generally correspond to the advantages of corresponding methods.

Further preferred embodiments and advantages emerge from the dependent claims and the figures.

BRIEF DESCRIPTION OF THE DRAWINGS

Below, the invention is described in more detail by means of examples and the included drawings. The figures show.

The reference symbols used in the figures and their meaning are summarized in the list of reference symbols. The described embodiments are meant as examples and shall not confine the invention.

DETAILED DESCRIPTION OF THE INVENTION

Figure 1:
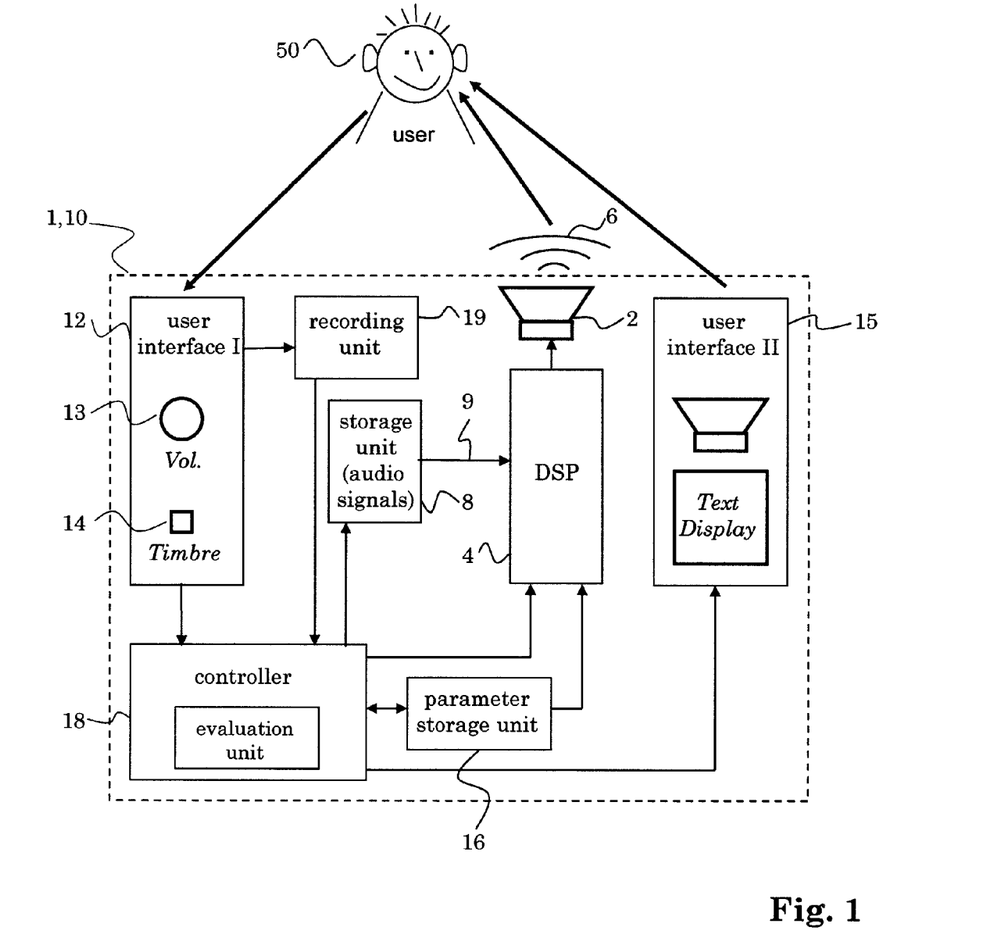
FIG. 1 a diagrammatical illustration of an arrangement according to the invention.

FIG. 1 shows a diagrammatical illustration of an arrangement 1 for improving a hearing system user's ability to make use of one or more adjustable audio processing parameters of said hearing system comprising a hearing device 10. Said hearing system user is labelled 50. In the example of FIG. 1, the arrangement 1 is identical with the hearing system 10. The constituents of the arrangement 1 can be distributed in different manners among different constituents of the hearing system 10 (if the hearing system 1 comprises more than one device). The whole arrangement may even be comprised in one hearing device.

The arrangement 1 comprises a control unit 18, a sound generating unit 2, a first user interface 12, a signal processing unit 4, a parameter storage unit 16 and a storage unit 8 comprising data representative of audio signals 9. In the example of FIG. 1, the arrangement 1 furthermore comprises a recording unit 19 and an optional second user interface 15.

Control unit 18 is operationally connected to each of the constituents of the arrangement 1 mentioned above.

User interface 1 comprises user controls 13,14, which are manipulable by user 50, e.g., as indicated in FIG. 1, for adjusting the general output level (volume) and the timbre of sound played to the user. User interface 1 converts user input into signals fed to control unit 18, which interprets manipulations of user controls 13,14 and controls signal processing unit 4 in dependence of said user input. Typically, one or more audio processing parameters, which can be stored in parameter storage unit 16, are selected and adjusted in dependence of said user input.

In order to get user 50 acquainted with adjustable audio processing parameters of hearing system 1, in particular with those, which can be adjusted using first user interface 12, in particular user controls 13 and 14, a method for improving the user's ability to make use of these adjustable audio processing parameters can be carried out by means of arrangement 1. For carrying out such a method, storage unit 8 comprises data representative of audio signals 9, which are representative of test sounds. Control unit 18 controls storage unit 8, signal processing unit 4 and sound generating unit 2 in such a way, that test sounds are played to user 50 as signals 6 to be perceived by user 50.

For example, firstly, a first test sound is played to user 50. Then, a second test sound is played to user 50. Said second test sound is, e.g., a modified version of said first test sound. Preferably, said second test sound is obtained by feeding the same audio signals to signal processing unit 4 as are used for generating said first test sound, while differently processing these audio signals in signal processing unit 4 (due to differently adjusting at least one audio processing parameter), and converting the so-obtained audio signals in sound generating unit 2 into perceivable signals 6. It is nevertheless also possible to have data representative of audio signals representative of first and, in addition, data representative of audio signals representative of second test sounds stored, e.g., in storage unit 8. If, e.g., said first test sound has been obtained by adjusting one specific audio signal processing parameter (which can be a specific group of audio signal processing parameters), this specific audio signal processing parameter is preferably comprised in the choice of sound modification possibilities offered to the user. This enables the user to achieve a full compensation of the modifications, which have been carried out for obtaining said second test sound from said first test sound.

Said at least one audio processing parameter can be, e.g., one of the group comprising the general output level, a dynamics compression parameter such as a compression ratio or a level above which signals are compressed, a filtering parameter such as a cutoff frequency or a filtering slope, a parameter controlling the degree of noise cancelling, a beam former parameter such as the opening angle of the beam or an angle indicating the direction of the beam, or a combination of any of these parameters, possibly also with other parameters. For example, a combination or group of parameters could be set up for achieving an improved speech intelligibility, e.g., by involving the general output level and compression parameters and filtering parameters.

After having perceived said first and said second test sounds, user 50 selects from a choice of audio processing parameters that one of these audio processing parameters, which user 50 expects to be most promising for modifying said second test sound towards said first test sound. I.e., user 50 selects and manipulates user controls of user interface 12 for undoing the differences between said first test sound and said second test sound as well as possible.

If user 50 is already well trained, he will manipulate the user controls such, that exactly that one or more parameters are adjusted, which are responsible for the difference between said first and said second test sounds. If user 50 is already well trained, he will furthermore manipulate the user controls such, that the correspondingly-modified second test sound strongly resembles said first test sound or is optimally identical therewith.

This playing first and second test sounds and receiving user input for achieving a resemblance between these can preferably be repeated many times, for many or for all available adjustable audio processing parameters or groups of audio processing parameters. It is possible to do this with the same first test sound or with different first test sounds. In the latter case, storage unit 8 comprises data representative of different audio signals 9 convertible into different first test sounds. E.g., there could be first test sounds with a strong high-frequency portion, first test sounds with a strong low-frequency portion, first test sounds having strongly varying dynamics and so on.

The user's manipulations of user interface 12 can be recorded in recording unit 19. The so-recorded data can be analyzed in an evaluation unit 17 of control unit 18. This allows to monitor the user's ability to adjust adjustable audio processing parameters properly and/or the user's learning progress.

On the one hand, it can be monitored, whether or not user 50 knows, which parameter or group of parameters has to be adjusted in order to achieve a desired change in a perceived sound. On the other hand, it can be monitored, if user 50, once having chosen a parameter or group of parameter, makes adjustments in an efficient manner. For example, the results achieved when one firstly "over-corrects" (or "over-compensates"), and then further adjusts towards the aimed-at sound, are usually better than the results one achieves when one makes slow adjustments only towards the aimed-at sound, while not exceeding the optimal adjustment, because in the latter case, the final adjustment is typically still far from the optimum adjustment.

Evaluation unit 17 can calculate a value or several values representative of the user's abilities, be it concerning the user's ability to choose appropriate audio processing parameters and/or be it concerning the user's ability to make adjustments effectively. Such values can be obtained, e.g., from a comparison of what the user has chosen to do to an expectation.

In dependence of said value or values, appropriate actions can be taken. E.g., the user 50 can be informed that he performed well or poorly; or the value(s) can be used as a diagnostic value, possibly indicating that user 50 is mentally incapable of benefitting from such a training; or, the value(s) can be used to decide that user 50 would be better off switching into an automatic mode, in which the user does not (or hardly) have to make sound modifications; or, the value(s) can be used to decide that user 50 would be better off using a different hearing system.

Messages and information can be transferred to user 50 via second user interface 15, which may comprise sound generating unit 2, and which may comprise an optical display and/or an acoustic output.

A method corresponding to a method described above is illustrated in FIG. 2.

Figure 2:
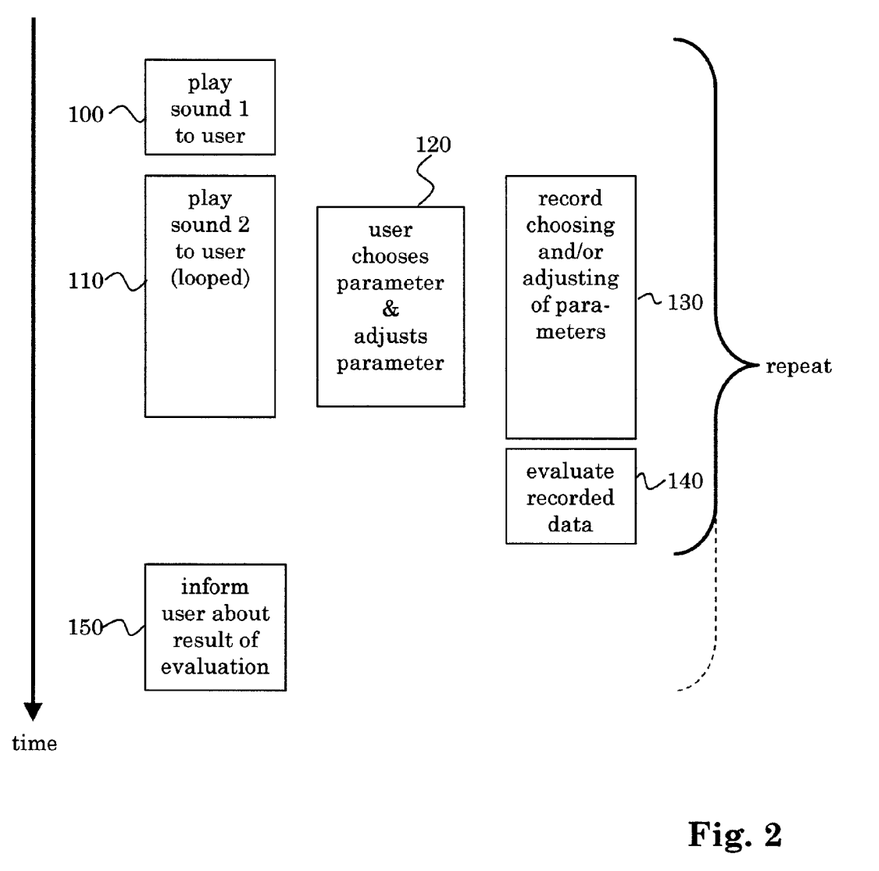
FIG. 2 a schematical illustration of a method according to the invention.

FIG. 2 shows a schematical illustration of a method for improving a hearing system user's ability to make use of one or more adjustable audio processing parameters of the hearing system. The hearing system and arrangement may, e.g., be one as shown in FIG. 1. The time axis is on the left.

Firstly, a first test sound is played to the hearing system user (step 100). Then, a second test sound is played to the hearing system user, usually in a looped/repeated manner (step 110). Preferably while listening to this second test sound, the user selects an audio processing parameter (which can be a combination of several other audio processing parameters) and makes adjustments for achieving modifications to said second test sound, with the aim to make it resemble said first test sound (step 120). The user's actions are recorded (step 130). When the user has finished adjusting, the recorded data are evaluated (step 140).

All this may be repeated several times, and finally the user is informed about the results (step 150); and/or the user is informed about the results already after each evaluation (step 150).

Several refinements of the method are possible. E.g., the user can be informed about his task (cause sound modifications for making the secondly-played sound resemble the firstly-played sound) before step 100; and/or the first test sound could be replayed to the user (e.g., on demand) during step 120.

It is possible to provide the user with an introductory exercise before step 100. This can comprise the steps of
  selecting at least one audio processing parameter (by the user or by the arrangement); and
  playing a test sound to the user; and
  asking the user to adjust said selected at least one audio processing parameter for modifying said test sound; and/or
  adjusting said selected at least one audio processing parameter (by the user or by the arrangement).

This allows the user to perceive the sound modification caused by said selected at least one audio processing parameter. If the user makes the parameter adjustments by himself, usually he will later on much better remember the link between the selected parameter(s) and the corresponding changes in sound.

Figure 3:
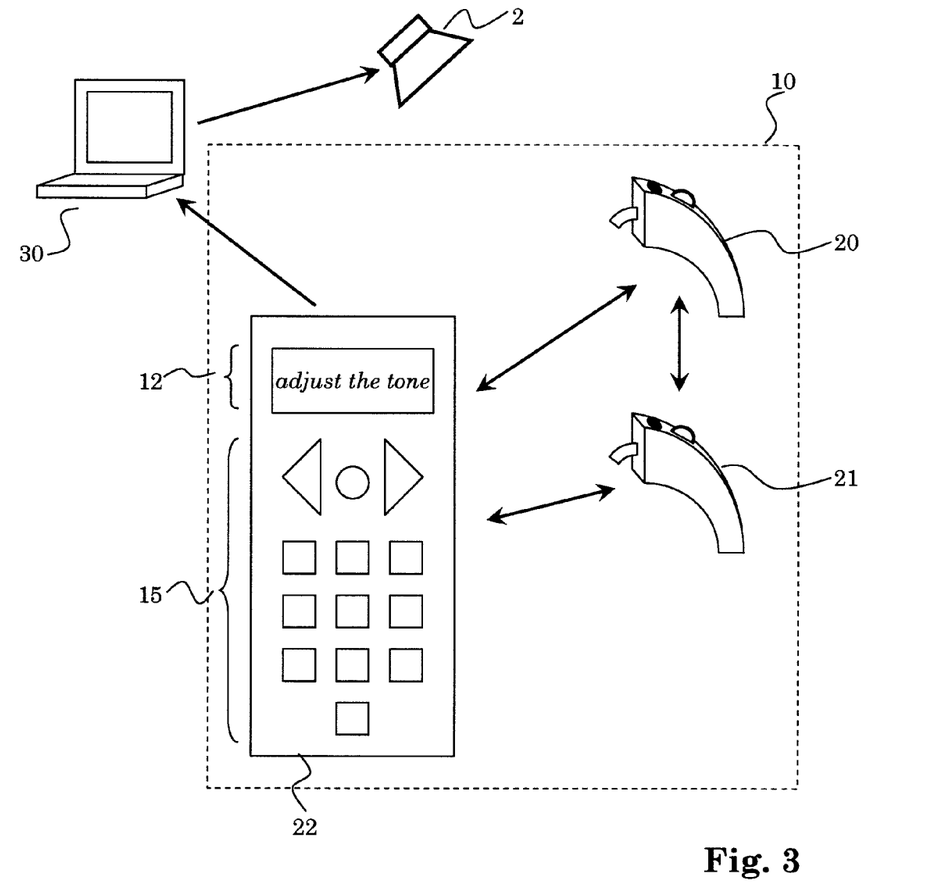
FIG. 3 a diagrammatical illustration of an arrangement according to the invention.

FIG. 3 shows a diagrammatical illustration of another arrangement 1 for improving a hearing system user's ability to make use of one or more adjustable audio processing parameters of said hearing system. In this embodiment, the arrangement 1 comprises, besides the hearing system 10, a computer 30 operationally connected to the hearing system 10, and a sound generating unit 2 operationally connected to said computer 30.

The hearing system 10 comprises two hearing devices 20,21 and a remote control 22. The constituents of the arrangement 1 can be the same as in the embodiment of FIG. 1, and they may be distributed in different ways among the devices 20,21,22 of the hearing system 10 and the computer 30. In particular, the first user interface 12 can be provided in remote control 22 and/or in hearing devices 20,21. And the second user interface 15 can be provided in remote control 22 and/or in computer 30. While in the embodiment of FIG. 1, it was possible that the sound generating unit 2 was identical with the receiver of a hearing device, in the embodiment of FIG. 3, the sound generating unit 2 is definitely different from the receiver of one of the hearing devices 20,21. A computer program product for implementing the invention can be run fully or in part in one of the constituents 20,21,22 of the hearing system 10 and/or fully or in part in computer 30.

Figure 4:
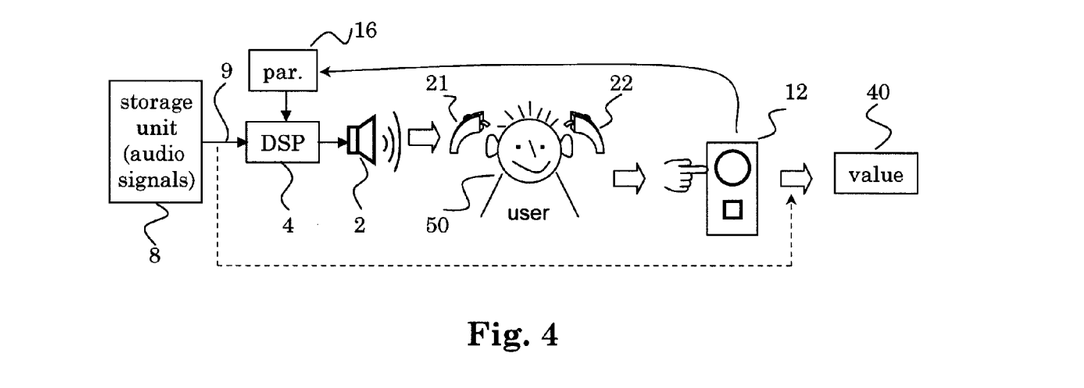
FIG. 4 a diagrammatical illustration of a method and an arrangement according to the invention.

FIG. 4 is a diagrammatical illustration of a method and an arrangement according to the invention. User 50 wears two hearing devices 21,22 belonging to his hearing system. External from hearing devices 21,22, a storage unit 8 comprising data representative of test audio signals, a signal processing unit 4, a storage unit 16 comprising audio processing parameters and a sound generating unit 2, e.g., a loudspeaker 2, are provided. A user interface 12 can be comprised in the hearing system or, rather, be external to the hearing system.

For instance, the following method can be carried out by the arrangement illustrated in FIG. 4: From storage unit 8, test audio signals 9 are fed to signal processing unit 4, in which test audio signals 9 are subject to processing, wherein audio signal processing parameters with settings as provided by storage unit 16 are used. The correspondingly processed audio signals are fed to sound generating unit 2, so as to generate test sounds (sound waves). User 50 perceives said test sounds via his hearing devices 21,22. In reaction to said test sounds, user 50 will manipulate user interface 12, so as to cause an adjustment of at least one audio processing parameter, i.e. to change the setting of at least one audio processing parameter used for processing said test audio signals 9.

At least one value 40 is then obtained in dependence of the audio processing parameter adjustment caused by user 50 and in dependence of the test audio signal 9 played to user 50.

In dependence of said at least one value 40, information can be communicated to user 50, e.g., a (visual or acoustic) message such as "you should have chosen the timbre knob" or "you are doing very well" or "this test will be repeated, listen closely".

Figure 5:
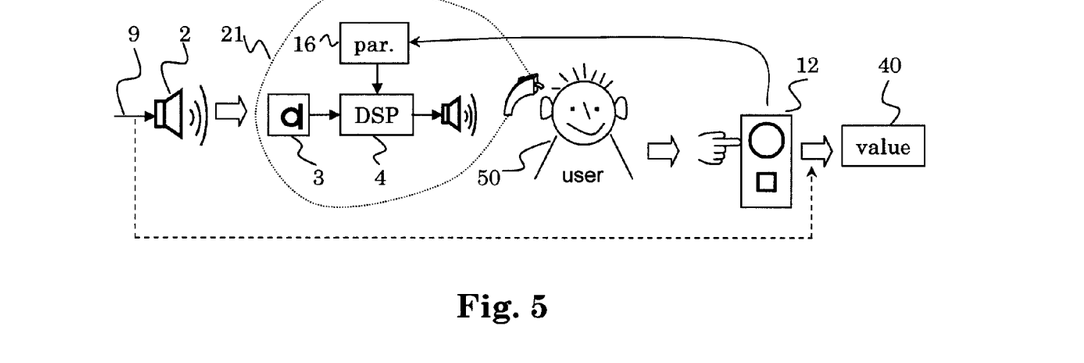
FIG. 5 a diagrammatical illustration of a method and an arrangement according to the invention.

FIG. 5 is a diagrammatical illustration of a method and an arrangement according to the invention. In this embodiment, test audio signals 9 are fed to a sound generating unit 2 external to a hearing device 21 worn by user 50, so as to generate test sounds to be played to user 50. Hearing device 21 comprises an input transducer 3, a signal processor 4, a storage unit 16 comprising audio processing parameters and a loudspeaker, also referred to as receiver. Within hearing device 21, the test sounds are picked up by input transducer 3 and processed in signal processor 4 according to audio processing parameter settings received from storage unit 16. The processed audio signals are then converted into sound by said receiver. In reaction to the test sounds played to user 50, user 50 will manipulate user interface 12, which preferably is comprised in the user's hearing system, e.g., in hearing device 21 or in a remote control. Said manipulation causes changes in the settings of at least one audio processing parameter in storage unit 16, and the processing in signal processor 4 is adjusted accordingly.

At least one value 40 is then obtained in dependence of the audio processing parameter adjustment caused by user 50 and in dependence of the test audio signal 9 played to user 50.

In dependence of said at least one value 40, information can then be communicated to user 50.

The test audio signals 9 in FIG. 5 can, e.g., be obtained directly from a storage unit or be obtained similar to the audio signals fed to the sound generating unit 2 as shown in FIG. 4, i.e. they can be subject to signal processing in a signal processing unit first.

In one embodiment, which is not shown in FIG. 4 or FIG. 5, the generation and conversion and optional processing of test audio signals takes place within the hearing system, e.g., within a hearing device. Such an embodiment has the advantage that the corresponding arrangement is very small and needs very little space and no room with a particular installation. In such an embodiment, the hearing system can allow the user to carry out a method according to the invention without using auxiliary means. But with respect to such an embodiment, the embodiments of FIGS. 4 and 5 have the advantage that a more realistic scenario is used for training the usage of adjustable audio processing parameters, since test sounds are provided from outside the user's hearing devices and, accordingly, test sounds are perceived by user 50 in the way normal sound during normal use of the hearing system is perceived, which includes, that, besides sound that ran along the "electrical path" (microphone—signal processor—receiver), also sound is received that bypasses the "electrical path", e.g., through a vent of a hearing device or by bone conduction.

Methods according to the invention can be of particular value when applied
  before a fitting of the hearing system to the user's hearing preferences; this allows the user to get acquainted to the hearing system, in particular to its adjustable parameters and to adjusting said parameters; and/or after a fitting, possibly after a fine-tuning, of the hearing system to the user's hearing preferences; this can enable the user to further optimize the performance of his hearing system; and/or during the first weeks or months of using the hearing system; this can reduce the time needed for acclimatization, because the user can readjust the sound and general output level of his hearing system practically any time.

When a hearing system user receives a new hearing device, which shall provide for an amplification of acoustic signals to a loudness much higher than what the user perceived before, it is necessary to firstly use a rather small amplification gain and later on, in several steps, increase that amplification gain to a reasonable final value, because otherwise, the user's hearing experience in the beginning would be unpleasant, because sound would be perceived much too loud. This effect is known as "acclimatization effect".

Methods according to the invention can improve the user's understanding of how to use sound modification possibilities provided by the hearing system. In particular, the user can be trained to select the most appropriate sound modification possibility; and the user can be trained to use modification possibilities in a suitable way.

LIST OF REFERENCE SYMBOLS 1 arrangement
2 sound generating unit, transducer, output transducer, loudspeaker
3 input transducer, microphone
4 signal processing unit, digital signal processor, DSP
6 signals to be perceived by the user
8 storage unit, storage unit comprising data representative of audio signals
9 audio signals representative of test sounds, test audio signals
10 hearing system
12 user interface, set of user controls
13 user control, wheel, volume wheel
14 user control, knob
15 user interface, information output, display
16 parameter storage unit, storage unit comprising audio processing parameters, parameter memory
17 evaluation unit
18 control unit, controller
19 recording unit, recorder for recording user input
20 hearing device
21 hearing device
22 remote control
30 computer
40 value
50 user, hearing system user
100-150 steps

What is claimed is:

1. Method comprising the steps of
a) playing a first test sound to a user (50) of a hearing system (10);
r) receiving user input from said user in reaction to step a);
s) interpreting said user input as a request for selecting and/or adjusting at least one audio processing parameter of a signal processing unit (4);
h) calculating—based on said request obtained in step s), and in dependence of said first test sound played to said user (50)—at least one value representing said user's ability to one or both of:
correctly choose one or more appropriate user-adjustable audio processing parameters of said hearing system (10), and
correctly adjust one or more user-adjustable audio processing parameters of said hearing system (10),
wherein the at least one value representing said user's ability is calculated by comparing the received user input to an expected user input.

2. Method comprising the steps of
a) playing in a first test sound to a user (50) of a hearing system (10);
r) receiving user input from said user in reaction to step a);
s') selecting and/or adjusting at least one audio processing parameter of a signal processing unit (4) in response to said user input;
h') calculating—based on said selection and/or adjustment according to step s'), and in dependence of said first test sound played to said user (50)—at least one value representing said user's ability to one or both of:
correctly choose one or more appropriate user-adjustable audio processing parameters of said hearing system (10), and
correctly adjust one or more user-adjustable audio processing parameters of said hearing system (10),
wherein the at least one value representing said user's ability is calculated by comparing the received user input to an expected user input.

3. The method according to claim 1 wherein said first test sound is generated by a sound generating unit (2) external to said hearing system.

4. The method according to claim 1 comprising the step of
x) maladjusting at least one parameter of the signal processing unit (4) of said hearing system (10) for letting said user (50) perceive a distorted version of said first test sound.

5. The method according to claim 1 comprising the step of
b) playing a second test sound to said user (50);
wherein said user input is received in reaction to step a) and step b).

6. The method according to claim 5, comprising the step of
q) minimizing differences between said first and second test sound by said adjusting said at least one audio processing parameter mentioned in step s).

7. The method according to claim 1 comprising the steps of
p) processing said first test sound in the signal processing unit (4) mentioned in step s), using the at least one audio processing parameter mentioned in step s) adjusted as mentioned in step s); and
d) playing the correspondingly processed first test sound to said user (50).

8. The method according to claim 1 comprising the step of
k) providing said user (50) with information, which depends on said at least one value mentioned in step h).

9. Use of a method according to claim 1 for improving said user's ability to make use of the one or more user-adjustable audio processing parameters of said hearing system (10).

10. The method according to claim 1, further comprising the step of providing said user (50) with performance level information of the user in correctly choosing the one or more appropriate user-adjustable audio processing parameters or correctly adjusting the one or more user-adjustable audio processing parameters, depending on said at least one value representing said user's ability.

11. The method according to claim 1, further comprising the step of diagnosing said user (50) based on said at least one value representing said user's ability.

12. The method according to claim 1 or claim 2, wherein
said hearing system (10) is used for generating said first test sound; and/or
said user input is received by a user interface (12) of said hearing system (10); and/or
said at least one parameter of said signal processing unit (4) is adjusted in response to said user input, wherein said signal processing unit (4) is comprised in said hearing system (10); and/or
at least one audio processing parameter of said signal processing unit (4) of said hearing system (10) is adjusted for generating said first test sound.

13. Arrangement (1) comprising
a hearing system (10);
a sound generating unit (2) adapted to playing at least one test sound to a user (50) of said hearing system (10);
a signal processing unit (4) controllable by at least one adjustable audio processing parameter, for processing audio signals (9);
a first user interface (12) adapted to receiving user input from said user (50) in reaction to said playing of said at least one test sound;
an evaluation unit (17) adapted to interpreting said user input as a request for selecting and/or adjusting said at least one audio processing parameter of said signal processing unit (4), and adapted to calculating—based on said request, and in dependence of said at least one test sound played to said user (50)—at least one value representing said user's ability to one or both of:
correctly choose one or more appropriate user-adjustable audio processing parameters of said hearing system (10), and
correctly adjust one or more user-adjustable audio processing parameters of said hearing system (10),
wherein the at least one value representing said user's ability is calculated by comparing the received user input to an expected user input.

14. The arrangement (1) according to claim 13, wherein said hearing system (10) comprises at least one of
said sound generating unit (2);
said first user interface (12);
said signal processing unit (4) controllable by said at least one adjustable audio processing parameter.

15. The arrangement according to claim 13, comprising a control unit (18) adapted to converting said user input into adjustments of at least one audio processing parameter of said signal processing unit (4).

16. The arrangement according to claim 13, comprising a storage unit (8) for storing data representative of audio signals (9) from which said at least one test sound is obtainable.

17. The arrangement according to claim 13, comprising a control unit (18) adapted to maladjusting at least one parameter of said signal processing unit (4) of said hearing system (10) for letting said user (50) perceive a distorted version of said at least one test sound.

18. The arrangement according to claim 13, comprising a control unit (18) adapted to controlling at least said sound generating unit (2) in such a way, that first, a first test sound is played to said user (50) and then, a second test sound is played to said user (50).

19. The arrangement according to claim 18, wherein said second test sound is obtained by adjusting at least one audio processing parameter of said signal processing unit (4) of said arrangement (1) and processing audio signals (9) in that signal processing unit (4).

20. The arrangement according to claim 18, comprising a second user interface (15), which may be identical with said first user interface (12) and/or may comprise said sound generating unit (2), for providing said user (50) with information advising said user (50) to minimize differences between said first and said second test sound by said adjusting said at least one adjustable audio processing parameter of said signal processing unit (4).

21. The arrangement according to claim 13, comprising a third user interface (15), which may be identical with said first user interface (12) and/or with a second interface (15) and/or may comprise said sound generating unit (2), for providing said user (50) with information, which depends on said at least one value.

22. The arrangement (1) according to claim 13, which is fully integrated in said hearing system (10).

23. The arrangement (1) according to claim 13, wherein said sound generating unit (2) is external to said hearing system (10).

* * * * *

UNITED STATES PATENT AND TRADEMARK OFFICE
CERTIFICATE OF CORRECTION

PATENT NO. : 8,666,084 B2
APPLICATION NO. : 12/667244
DATED : March 4, 2014
INVENTOR(S) : Michael Boretzki It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1034 days.

Signed and Sealed this
Twenty-ninth Day of September, 2015

Michelle K. Lee
*Director of the United States Patent and Trademark Office*